United States Patent [19]

Rosenberg

[11] Patent Number: 4,689,228

[45] Date of Patent: Aug. 25, 1987

[54] ENHANCED ABSORPTION OF DIETARY MINERAL COMPONENTS

[75] Inventor: Irwin H. Rosenberg, Chicago, Ill.

[73] Assignee: University Patents, Inc., Westport, Conn.

[21] Appl. No.: 769,533

[22] Filed: Aug. 26, 1985

[51] Int. Cl.$^4$ ..................... A61K 33/06; A61K 33/14; C08B 37/16
[52] U.S. Cl. ..................................... 424/153; 536/103
[58] Field of Search ................. 424/153, 154; 536/103

[56] References Cited

PUBLICATIONS

Chem. Abst. 91 (1979) 156315w.

Primary Examiner—Stanley J. Friedman
Attorney, Agent, or Firm—Philip Hill

[57] ABSTRACT

Food supplement compositions for the enhanced absorption of nutrient mineral components additionally include a complex carbohydrate fraction, having an average molecular weight in the range from about 750 to about 3500, and a suitable carrier agent. The compositions are particularly includable in the diets of subjects who have a shortened interstinal length and need additional absorption of calcium and other mineral elements.

11 Claims, 1 Drawing Figure

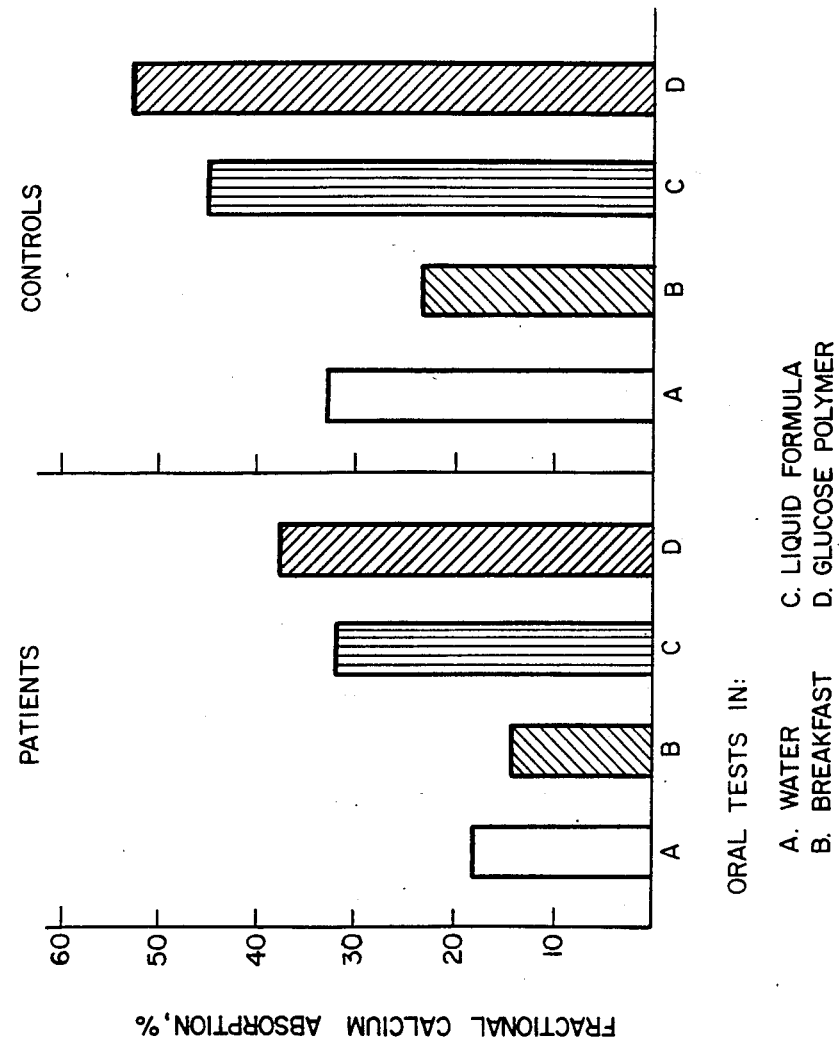

ENHANCED ABSORPTION OF DIETARY MINERAL COMPONENTS

BACKGROUND OF THE INVENTION

Various diet components, including fats, fibers, and carbohydrates, have been known to affect the absorption of mineral components in the human digestive system. Most attention has been given to calcium balance in the system, in part because of its relationship to the development and maintenance of good bone structure. Mineral components are largely absorbed in the intestinal area, and, where a person has, for example, been afflicted with Crohn's disease, or experienced intestinal resection or jejunoileal bypass, decreased calcium absorption is regularly observed. Although other mineral nutrients have been less well studied, similar phenomena do occur. Accordingly a distinct dietary problem exists in subjects having diminished enteral absorption capacity. A similar need for enhanced absorption of dietary mineral components, especially including calcium, exists in infant diet formulas, where provision for developing an adequate bone structure is critical.

Improved calcium nutrition may be achieved by developing dietary factors that increase the efficiency of absorption. Such factors would be operative in all subjects but particularly effective in subjects having shortened intestinal length.

With particular reference to the absorption of calcium, vitamin D, lactose, and certain amino acids are known to enhance absorption, while phytate, oxalate, and cellulose have been shown to decrease absorption. Recent studies of carbohydrates have produced both positive and negative results under a variety of test conditions. Although the use of lactose, a disaccharide, would appear promising, many subjects are intolerant of this sugar so that its application to this type of problem has not been strongly suggested or pursued.

Applicants have made the unexpected discovery that use of a complex carbohydrate material, essentially a low polymer including simple sugar units, together with a calcium component, or other mineral component, surprisingly enhances the assimilation of the calcium, or other mineral, component. Reports of experimental studies, on both human and animal subjects, have been presented in *Gastroenterology*, 87, 596–600 (1984); *Clinical Research*, 32, 740A (1984); and *Am. J. Clinical Nutrition*, 41, 243–5 (1985).

SUMMARY OF THE INVENTION

This invention relates to food supplement compositions, for the enhanced absorption of calcium and other dietary mineral components in human subjects. Such compositions broadly comprise one or more mineral components, a complex carbohydrate of an intermediate average molecular weight generally within the range from about 750 to about 3500, most preferably from about 1000 to about 1500, and a carrier agent for the mineral and carbohydrate components.

This invention particularly relates to the absorption of calcium ion when employing an ingested mixture of a calcium salt and a glucose polymer, preferably a partially hydrolyzed cornstarch.

This invention similarly relates to food supplement compositions for the enhanced absorption of other mineral components, including salts of magnesium, zinc and related nutrient materials.

The compositions of this invention may be formulated in pill, or other solid, form, as a syrup or gel, or in a relatively dilute aqueous solution.

The compositions of this invention, while useful in any dietary regimen, are particularly valuable for subjects having disorders of the gastrointestinal tract, particularly those with short bowel, who are at increased risk of developing vitamin D depletion, calcium malabsorption, and metabolic bone disease.

DESCRIPTION OF THE INVENTION

This invention relates broadly to food supplement compositions intended for the enhanced absorption of nutrient dietary mineral materials, particularly in the intestinal tract of humans. The food supplement compositions of this invention comprise at least one or more mineral components, a complex carbohydrate material having a molecular weight within the range from about 750 to about 3500, and a suitable carrier agent.

In the compositions of this invention, the dietary mineral component is preferably selected from among the compounds of calcium, magnesium, strontium, barium, zinc, cadmium, and mixtures of any two or more of these. Considering the need for solubility in water and gastric juices, preferred compounds are the water-soluble salts or compounds readily converted to water-soluble salts in the digestive tract. In the case of calcium, the chloride and acetate salts are preferred although the carbonate and bicarbonate are readily converted to such salts following ingestion. Strongly acidic or alkaline compounds, such as calcium oxide, should be avoided because of undesirable side effects. Other preferred components are the suitable compounds of magnesium and zinc. Although in most embodiments of this invention, the supplement composition will be intended to treat the absorption of one particular metal or mineral component, mixtures of such metal or mineral components may be employed to broaden the effectiveness of the selected food composition.

The complex carbohydrate of the food composition of this invention is desirably a glucose polymer, although other carbohydrate polymers of suitable molecular weight may be employed. These polymers include, for example, corn syrup solids, maltodextrins, cyclodextrins, and high-amylose starch. While suitable average molecular weights of the complex carbohydrates of this invention lie generally within the range from about 750 to about 3500, preferred carbohydrates have a molecular weight within the range from about 1000 to about 2500, most preferably from about 1000 to about 1500. A particularly desired glucose polymer is a partially hydrolyzed cornstarch, a homopolysaccharide consisting primarily of repeating alpha (1–4)-linked D-glucose units. In the gastrointestinal tract any selected carbohydrate polymer will be further hydrolyzed by the action of either amylase or an oligosaccharidase to its constituent monosaccharide.

The carrier agent of the food composition of this invention may be a solid or liquid dietary formula, water, or a gel, so that the concerted composition may be in the physical form of a pill, capsule, syrup, gel, or a dilute, aqueous liquid. The composition of this invention is suitably packaged in any convenient form, related to the selected dosage of the food composition.

In the practice of this invention the dosage of the food composition may be selected to include in the supplement unit from about 2 to about 40 grams of complex carbohydrate, preferably from about 10 to about 30 grams. When employing water as the carrier agent, the molarity of the complex carbohydrate should be within the range from about 0.001 to about 0.15, preferably from about 0.002 to about 0.13. In any event, it is desired that the solution in the intestinal tract be about 0.004 molar in complex carbohydrate.

The dosage unit of the mineral component in the supplement unit will vary with the selection of the mineral. For example, a preferred dosage range for a calcium compound is from about 100 to about 1000 milligrams; for a magnesium compound from about 50 to about 500 milligrams; and for a zinc compound from about 5 to about 50 milligrams.

A desirable food supplement unit of this invention comprises from about 100 to about 500 milligrams, preferably about 200 milligrams, calcium chloride; from about 5 to about 40 grams, preferably about 10 grams, of a partially hydrolyzed corn starch fraction, having an average molecular weight within the range from about 1200 to about 2000; and from about 200 to about 1000 milliliters of distilled water.

The following is exemplary, without limitation, of the food supplement compositions of this invention and their utility.

EXAMPLE I

An extensive study was conducted with both patients and normal controls to determine the effect of diet variance on calcium absorption.

Twelve patients (eight women and four men) with a history of intestinal resection for Crohn's disease or jejunoileal bypass for massive obesity underwent calcium absorption studies. Patients were neither selected nor excluded on the basis of sex, history of past or concurrent vitamin D or corticosteroid therapy, or history of lactose intolerance. Patients older than 65 years of age were, however, excluded from this study. The twelve patients included nine with Crohn's disease (aged 23-62 years) and three with jejunoileal bypass (aged 32-36 years). Three patients were receiving vitamin D at the time of this study; however, no patient was receiving calcium supplements. The patients with Crohn's disease were ambulatory and were either in clinical remission or were well controlled with medication.

Fourteen normal controls (eight women and six men) whose ages ranged from 23 to 44 years underwent similar calcium absorption studies. None were taking vitamin D or calcium supplements.

Four test meals were employed: water, a standard breakfast, a liquid formula (Ensure, a product of Ross Laboratories), and a glucose polymer solution (Frodex-15, a product of Ross Laboratories).

During the study, the patients consumed their usual diets. Each subject was instructed in keeping a 3-day diet diary, from which calcium and phosphorus intakes were calculated.

Each patient or control was evaluated during a 2-3 week period. In the patient group, the mean dietary calcium intake was 616 mg (range 245-1039 mg) and mean dietary phosphate intake was 1122 mg (range 645-1871 mg). The mean dietary calcium intake in the control group was 657 mg (range 243-1075 mg) and mean dietary phosphate intake was 1153 mg (range 706-1121 mg).

$^{47}$Ca was administered orally on 4 separate days and intravenously on 1 day. After an overnight fast each subject was given 2 $\mu$Ci of $^{47}$Ca with one of the four test meals. The $^{47}$Ca was mixed in water containing 200 mg of elemental calcium, or in coffee with the breakfast, or directly in the Ensure or glucose polymer solution. The Ensure meal contained 200 mg calcium, and 200 mg phosphorus. Frodex-15, containing 40 g of carbohydrate-equivalent similar to the carbohydrate component of Ensure, was used to make a glucose polymer solution. To this glucose polymer solution, 200 mg of elemental calcium was added using CaCl$_2$. The subjects were then fasted for 4 hours after the dose and subsequently underwent arm counting at 4 hours thereafter. The tests were separated by 2-4 days.

Fractional calcium absorption was determined by measuring forearm radioactivity in a scintillation detector immediately before and at fixed intervals after the administration of the isotope.

The patient was positioned in a chair with the right forearm inserted in the counting chamber. The counting time was ~12-15 minutes (the error between successive counts was ±2.0%). Calcium absorption was then determined by measuring the ratio of the amount of radioactivity appearing in the forearm. To validate this technique for accurate measurement of fractional calcium absorption in patients with intestinal resection or bypass, arm counts were taken at 4 and 24 hours after tests in ten patients using different meals. No significant difference was seen in mean absorption at later time points as compared with 4-hour values.

DESCRIPTION OF DRAWINGS

FIG. 1 presents in graphical form results of dietary studies of patients and controls relative to this invention.

Results of these studies are summarized in FIG. 1. In patients with intestinal resection or bypass, mean fractional calcium absorption from CaCl$_2$ in water was 18.1%, a value significantly lower than controls. In ten patients fractional calcium absorption from the test breakfast was 14.4%, not significantly different from absorption with water. Fractional calcium absorption from liquid formula (Ensure) was 31.7% in six patients. In some patients calcium absorption increased 1.5- to 5-fold compared with breakfast. Patients with fractional absorption <20% from breakfast showed the most significant increase in calcium absorption with the liquid formula, whereas those with absorption >20% had minimal responses to liquid formula.

Two patients had calcium absorption studies done with the CaCl$_2$ administered along with glucose polymer at a dose similar to that present in Ensure (40 g). In one patient fractional absorption increased from 12% with breakfast to 35% with polymer. In the other patient absorption increased from 18% with water to 40% in the presence of glucose polymer.

Similar findings were observed in normal subjects. In the control group, fractional calcium absorption from water was 32.9%. With breakfast, fractional calcium absorption was 23.3%, not significantly different than absorption from CaCl$_2$ in water. Fractional calcium absorption from Ensure was 44.7% in six subjects, a significant increase over absorption from breakfast. Finally, absorption of CaCl$_2$ administered with glucose polymer was 50% and 54% in two subjects. Fractional calcium absorption increased from 10% to 50% in one and from 17% to 54% in the second as compared with breakfast.

EXAMPLE II

A study was conducted to determine the effect of glucose polymer (GP) in the diet on jejunal Ca and Mg absorption in eight normal subjects, using the triple-lumen intestinal perfusion technique. For each subject a 30 cm segment of jejunum was perfused for 60 minutes each with two test solutions containing: 50155 mM Ca, 5 mM Mg, 0.2 mM Zn, 50 mM Na, 5 mM K, 0.5% polyethylene glycol, and 0, 4 or 8 mM GP. In Study 1, absorptive flux was studied in four subjects receiving 0 and 4 mM GP. In Study 2, 4 subjects received 4 and 8 mM GP. The net flux rates ("+"=secretion, "−"=absorption) in the presence of different amounts of GP are shown in the following table.

|  | | Net Jejunal Flux Rate ($\mu$mol/30 cm/hr.) | | |
| --- | --- | --- | --- | --- |
|  | GP (mM) | H$_2$O (ml/30 cm/h) | Ca | Mg |
| Study 1 | 0 | −49 ± 11 | −90 ± 50 | +6 ± 50 |
|  | 4 | −111 ± 12 | −470 ± 90 | −400 ± 100 |
| Study 2 | 4 | −73 ± 10 | −560 ± 70 | −340 ± 60 |
|  | 8 | −60 ± 17 | −510 ± 130 | −350 ± 60 |

In Study 1, 4 mM GP doubled H$_2$O absorption, increased Ca absorption by 4-fold, and caused significant net jejunal uptake of Mg. In Study 2, no change in jejunal flux rates were observed when GP was increased from 4 to 8 mM. These results show that GP markedly enhances both Ca and Mg absorption in the jejunum.

We claim:

1. A food supplement composition, for the enhanced absorption of dietary minerals in the gastrointestinal tract of a human subject, each dosage unit thereof consisting essentially of:
   (a) from about 50 to about 1000 milligrams (a dosage unit) of a water-soluble dietary mineral component, selected from the class consisting of water-soluble compounds of calcium, magnesium, and mixtures thereof;
   (b) from about 2 to about 40 grams of a (complex) polymeric glucose carbohydrate, having a molecular weight within the range from about 750 to about 3500; and
   (c) water, as a carrier agent, to afford a polymeric glucose carbohydrate molarity in the dosage unit within the range from about 0.001 to about 0.15.

2. The composition of claim 1 wherein the dietary mineral component is a compound of calcium.

3. The composition of claim 1 wherein the dietary mineral component is a compound of magnesium.

4. The composition of claim 1 wherein the molecular weight of the carbohydrate is within the range from about 1000 to about 2500.

5. The composition of claim 4 wherein the molecular weight of the carbohydrate is within the range from about 1000 to about 2500.

6. The composition of claim 1 wherein the carbohydrate comprises a fraction of partially hydrolyzed cornstarch.

7. The food supplement of claim 1 wherein the dietary mineral component is a calcium compound and the amount thereof is within the range from about 100 to about 1000 milligrams.

8. The food supplement of claim 1 wherein the dietary mineral component is a magnesium compound and the amount thereof is within the range from about 50 to about 500 milligrams.

9. The food supplement composition of claim 1 wherein the molarity of carbohydrate is within the range from about 0.002 to about 0.13.

10. A food supplement composition unit, for the enhanced absorption of dietary minerals in a human subject, consisting essentially of:
    (a) from about 100 to about 500 milligrams calcium chloride;
    (b) from about 5 to about 40 grams of a partially hydrolyzed corn starch fraction, having an average molecular weight within the range from about 1200 to about 2000; and
    (c) from about 200 to about 1,000 milliliters of distilled water.

11. The food composition unit of claim 10, comprising about 200 milligrams calcium chloride, about 10 grams of the partially hydrolyzed cornstarch fraction, and about 200 milliliters of distilled water.

* * * * *